(12) United States Patent
Zhang et al.

(10) Patent No.: US 7,755,759 B2
(45) Date of Patent: Jul. 13, 2010

(54) METHODS AND SYSTEMS FOR EVALUATING PIGMENT DISPERSIONS

(75) Inventors: Lanhui Zhang, Webster, NY (US); Lin Ma, Webster, NY (US); Keith Wong, Vancouver, WA (US); Francisco Lopez, Rochester, NY (US); Robert Altavela, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 614 days.

(21) Appl. No.: 11/725,756

(22) Filed: Mar. 20, 2007

(65) Prior Publication Data

US 2008/0234975 A1 Sep. 25, 2008

(51) Int. Cl.
*G01N 15/02* (2006.01)
(52) U.S. Cl. ............... 356/335; 702/179; 356/337; 356/319; 356/441

(58) Field of Classification Search ......... 356/335–337, 356/319, 326, 441; 702/179
See application file for complete search history.

(56) References Cited

U.S. PATENT DOCUMENTS

| 6,917,424 B2 * | 7/2005 | Rodrigues et al. ........... 356/326 |
| 2004/0027569 A1 * | 2/2004 | Tucker ....................... 356/338 |

* cited by examiner

*Primary Examiner*—Gregory J Toatley, Jr.
*Assistant Examiner*—Iyabo S Alli
(74) *Attorney, Agent, or Firm*—Pillsbury Winthrop Shaw Pittman LLP

(57) ABSTRACT

Methods and systems for evaluating pigment dispersions with desired characteristics. More specifically, methods and systems for evaluating particle size of colorless or light color dispersions using a novel parameter described as particle size related scattering index (PSRSI).

16 Claims, 2 Drawing Sheets

FIG. 3
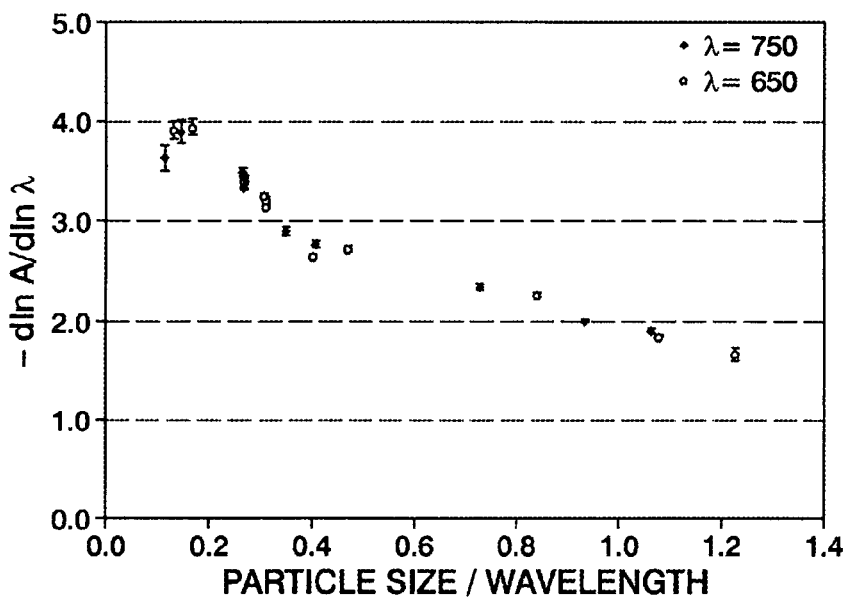
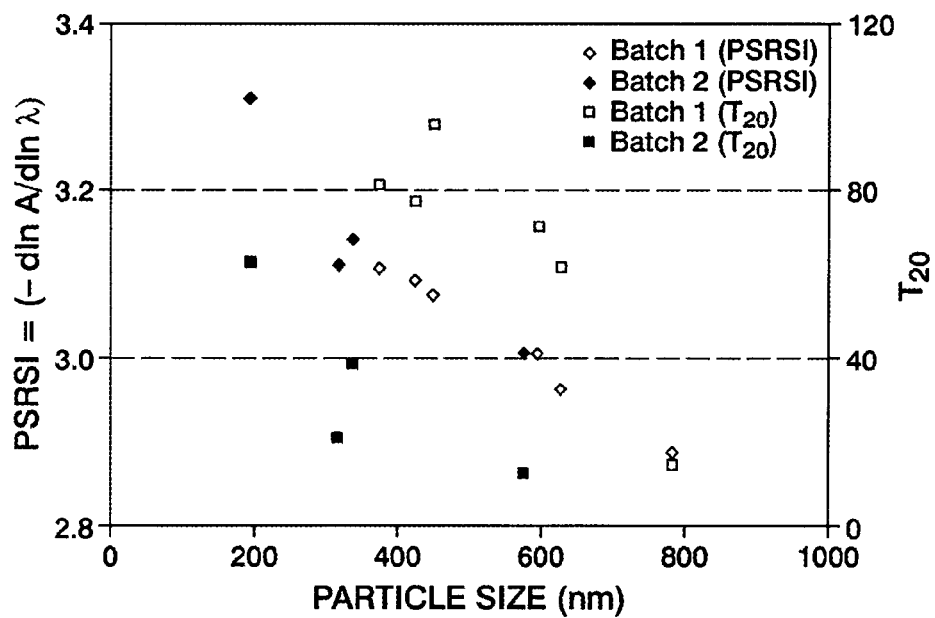
FIG. 4

METHODS AND SYSTEMS FOR EVALUATING PIGMENT DISPERSIONS

BACKGROUND

The presently disclosed embodiments are generally directed to methods and systems for evaluating and preparing pigment dispersions meeting specific desired characteristics. More specifically, the present embodiments are directed to methods for evaluating particle size of colorless or light color dispersions using a novel parameter described as particle size related scattering index (PSRSI) to determine particle size and distribution characteristics.

Methods for evaluating the characteristics of pigment dispersions are important for determining whether the evaluated dispersion has the target qualifications for a specific application. The methods may be used to monitor the preparation of dispersions or emulsions for use in a variety of applications, for example, in manufacturing particle dispersions, creams and lotions, emulsified oils, foods, cosmetics, cleaning fluids and precursors to many industrial products, such as coatings for photoreceptor layers. The general process of making ink involves the grinding of pigment in a device, such as a mill, to form a pigment dispersion, and subsequently letting down the pigment dispersion with suitable resins to meet certain rheological and functional properties. Thus, pigment selection and proper dispersion are of great importance to cost efficiency of making such products.

The dispersion process involves the breakdown of particles into smaller particles and their even distribution in a fluid, leading to a colloidal suspension. Pigment dispersion generally involves a complete wetting of the pigment particles, a breakdown of pigment particles, and stabilization of the dispersion to maintain a colloidal system during further processing or storage of the dispersion. Stabilization prevents the finely dispersed particles from reagglomerating or flocculating. The breakdown of pigment particles may be performed during the wetting process or mechanically by transferring mechanical energy into the system through special dispersing equipment. In some cases, particle dispersion can be prepared starting from solution by chemical reaction such as precipitation reaction or by physical change such as precipitation via solvent change. Emulsion dispersion can be formed either by dispersing and emulsifying liquid mixture or by chemical reaction such as emulsion polymerization.

The quality of the final dispersion, including particle dispersion and emulsion, is dependent on the optimization of many influencing factors. One of these factors is the size of the pigment particle or droplet. To achieve the optimum benefits of a pigment or emulsion, it is desirable to obtain a dispersion which particle size is as close to the target as possible.

As such, there have been different methods devised to evaluate dispersions for ensuring that the achieved dispersions have attained the desired characteristics. For example, a relative scattering index (RSI) is a commonly used parameter for evaluating colored pigment dispersions, which is defined as the absorbance ratio between the absorbance at a specific wavelength where the absorbance mainly reflects the contribution of light scattering, and the absorbance at the absorption peak where the absorbance is mainly the contribution of absorption.

RSI has been proven to be a good parameter for dispersion characterization and qualification that can be conveniently and quickly determined by a spectrophotometer. However, such a method is not applicable for colorless or light color dispersions where there is no absorption peak or where, at the peak wavelength, the contribution of light scattering to the apparent absorbance is not negligible since the RSI calculation requires such a peak absorbance to normalize the scattering signal. In colorless or light color dispersions, the contribution of absorption to the absorbance at the measuring wavelength is negligible as compared with the contribution of scattering.

Therefore, there is a need for a new method that can be used to efficiently and accurately evaluate and prepare colorless or light color dispersions that meet desired overall particle size and distribution properties, and a system that implements that method.

SUMMARY

According to embodiments illustrated herein, there are generally provided methods and systems for evaluating and preparing pigment dispersions meeting specific desired characteristics.

In particular, an embodiment provides a method for evaluating a colorless or light color pigment dispersion, comprising (a) preparing a pigment dispersion comprising colorless or light color particles in a fluid, (b) evaluating a spectrum of the pigment dispersion over a predetermined wavelength range by collecting transmission intensity at a fixed angle, (c) selecting a wavelength from the predetermined wavelength range wherein the selected wavelength $\lambda$ meets specific characteristics, and (d) calculating a particle size related scattering index of the pigment dispersion, wherein the particle size related scattering index is calculated from the following equation:

$$-(d \log A/d \log \lambda),$$

wherein A is an absorbance value of the pigment dispersion at the selected wavelength $\lambda$.

In yet other embodiments, there is provided a method for evaluating a colorless or light color pigment dispersion, comprising (a) preparing a pigment dispersion having known particle size and comprising a dispersion of colorless or light color particles in a fluid, (b) evaluating a spectrum of the pigment dispersion over a predetermined wavelength range by collecting transmission intensity at a fixed angle, (c) selecting a wavelength from the predetermined wavelength range wherein the selected wavelength $\lambda$ meets specific characteristics, (d) calculating a particle size related scattering index of the pigment dispersion, wherein the particle size related scattering index is calculated from the following equation:

$$-(d \log A/d \log \lambda),$$

wherein A is an absorbance value of the pigment dispersion at the selected wavelength $\lambda$, (e) building a calibration curve to correlate the particle size related scattering index and relative particle size (PS/$\lambda$) of the pigment dispersion, and (f) comparing a particle size related scattering index of a sample of the pigment dispersion having an unknown particle size against the calibration curve to determine the relative particle size of the sample.

Embodiments also provide a colorless or light color pigment dispersion prepared by using the above methods, or more specifically, prepared by monitoring the process using the particle size related scattering index of the pigment dispersion.

Further embodiments provide a system for evaluating particle size of a colorless or light color pigment dispersion; comprising a data carrier for carrying computer readable instructions, a computer for executing the computer readable instructions, and a spectrophotometer adapted to communicate with the computer for evaluating a spectrum of a pigment dispersion over a predetermined wavelength range by collecting transmission intensity at a fixed angle (e.g., fixed angle of 0° if a UV-Vis spectrophotometer is used), wherein the pigment dispersion is colorless or light color, and wherein the executed computer readable instructions cause the computer to receive the collected transmission intensity from the spectrophotometer for selecting a wavelength λ from the predetermined wavelength range based on the following characteristics (i) $0.1 < PS/\lambda < 1$, wherein PS is a particle size of interest, (ii) there is no absorption at or near the selected wavelength λ and apparent absorbance is due to light scattering of the pigment dispersion, (iii) the rate of apparent absorbance change with wavelength is not negligible at or near the selected wavelength λ, and (iv) the concentration of the pigment dispersion falls in a range for which apparent absorbance at the selected wavelength λ is from about 0.2 to about 2.0, calculate a particle size related scattering index of the pigment dispersion from the following equation:

$$-(d \log A/d \log \lambda),$$

wherein A is an absorbance value of the pigment dispersion at the selected wavelength λ, build a calibration curve to correlate the particle size related scattering index and relative particle size of the pigment dispersion, compare a particle size related scattering index of a sample of the pigment dispersion having an unknown particle size against the calibration curve to determine a relative particle size of the sample, and indicate the relative particle size of the sample.

BRIEF DESCRIPTION OF THE DRAWINGS

For a better understanding of the present embodiments, reference may be had to the accompanying figures.

FIG. 3 is a graph showing the PSRSI of mono-dispersed latex standards in aqueous solutions; and FIG. 4 is a graph showing a comparison of methods (PSRSI in dispersion versus $T_{20}$ of coated films).

DETAILED DESCRIPTION

Figure 1:
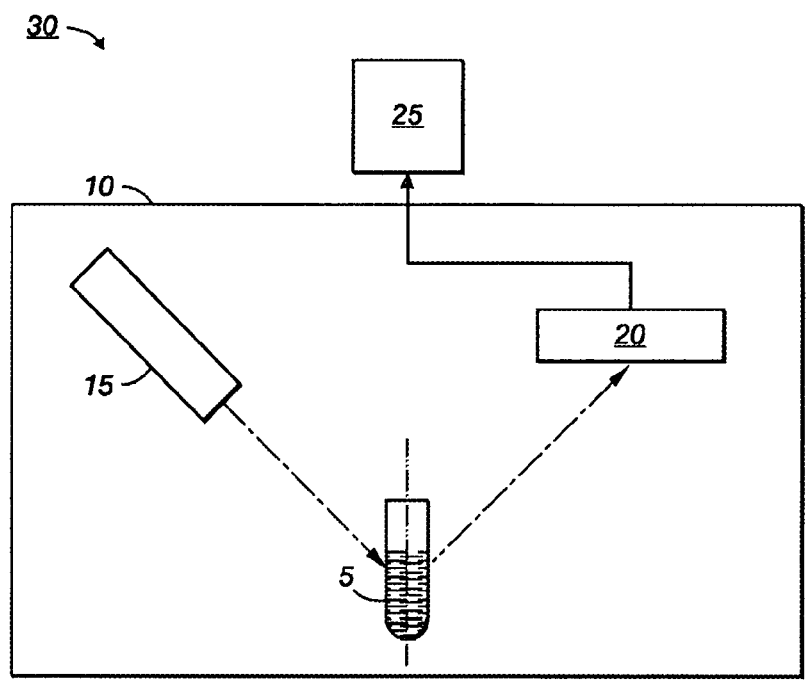
FIG. 1 is a schematic diagram of a system for determining a particle size related scattering index (PSRSI) for a pigment dispersion according to an embodiment of the present disclosure.

In the following description, it is understood that other embodiments may be utilized and structural and operational changes may be made without departure from the scope of the present embodiments disclosed herein.

The present embodiments propose a new parameter, Particle Size Related Scattering Index (PSRSI), for the characterization of the overall particle size and distribution properties of colorless or light color dispersion. The method and system employing this parameter is much faster, more convenient and more practically accessible than many of the alternative methods in evaluating and preparing colorless or light color pigment dispersions.

There have been different methods devised to evaluate dispersions for ensuring that the achieved dispersions have attained the desired characteristics. For example, a relative scattering index (RSI) is a commonly used parameter for evaluating colored pigment dispersions. RSI values are a relative score of particle size and distribution in a dispersion. The smaller the RSI, the lower the particle size. The RSI is defined as the absorbance ratio between the absorbance at a specific wavelength where the absorbance mainly reflects the contribution of light scattering, and the absorbance at the absorption peak, where the absorbance is mainly the contribution of absorption. The dispersion of a pigment material may be deemed acceptable when the RSI value is measured at a specific predetermined level.

RSI has been proven to be a good parameter for dispersion characterization and qualification that can be conveniently and quickly determined by a spectrophotometer. However, such a method is not applicable for colorless or light color dispersions where there is no absorption peak or where, at the peak wavelength, the contribution of light scattering to the apparent absorbance is not negligible. There are a number of colorless or light color dispersions that are of interest in photoreceptor and toner manufacture. These include, for example, dispersion undercoat (DUC) millbase, polytetrafluoroethylene (PTFE) dispersions and latex dispersions. The DUC is a ZnO dispersion used for undercoats, polytetrafluoroethylene (PTFE) dispersions are used in charge transport and anti-curl back coatings (ACBC) in photoreceptor, and latex dispersions for EA (Emulsion Aggregation) toner.

In the case of the DUC undercoat, the current method used to measure dispersion quality suffers from poor reproducibility and is slow. For example, the current procedure for DUC dispersion characterization/qualification, measures the transmissions and thicknesses of two dried coated films of different thickness at 950 nm and then interpolates transmission to a thickness of 20 microns ($T_{20}$) as a parameter for dispersion characterization and qualification. To enable a good interpolation, the thicknesses and the coating uniformities of the two films need to be well controlled. The whole process takes more than 1 hour. In addition, recent rheology studies showed that the microstructure of coated DUC films may be shear dependent, which may contribute to the current method not providing reproducible results. The thickness measurement is also not very accurate and therefore the accuracy of $T_{20}$ is not very high.

The present embodiments use the PSRSI to evaluate colorless or light color dispersions to determine whether the overall particle size and distribution properties of the dispersion meets a desired level or target particle size. A colorless or light color pigment is defined as one in which extinction coefficient at the visible wavelength is low. In colorless or light color dispersions, the contribution of light absorption to the apparent absorbance is negligible as compared with the contribution of light scattering. The PSRSI, m, is defined as and can be calculated from the following equations:

$$m = -(d\ln A/d\ln \lambda) \text{ or}$$

$$m = -(d \log A/d \log \lambda) \quad (1)$$

where A is the apparent absorbance of dispersion at wavelength λ.

It is well known that the intensity of scattering light of a pigment dispersion is strongly particle size dependent. For a dispersion with particle size that is very small (e.g., $PS/\lambda < 0.1$), its scattering is predominantly Rayleigh scattering and the intensity of scattered light, $I_{sc}$, follows the equation:

$$I_{sc} = k/\lambda^m$$

where m is equal to 4, λ is wavelength, and k is a constant depending on the intensity of incident light, number of scatterers (concentration), polarizability (reflective index difference between scatterer and supporting media), distance from scatterer, and angle of scattered light relative to the incident light. For a dispersion with particle size that is larger than wavelength (PS/λ>1.0), its scattering is predominantly Mie scattering, where the intensity of scattered light is not strongly wavelength dependent. When the particle size falls in the range between these two extremes, it can be reasonably inferred that 0<m<4 and m is relative particle size (PS/λ) dependent and therefore m can be used as an index of particle size for dispersion characterization and qualification.

When scattering is the sole cause of energy loss of incident light, the overall absorbance observed by spectrophotometer can be written as:

$$A = -\log (I_t / I_0)$$
$$= -\log \left[ (I_0 - \sum I_{sc}) / I_0 \right]$$
$$= -\ln \left[ (I_0 - \sum I_{sc}) / I_0 \right] / 2.303$$
$$= -\ln \left[ 1 - \sum I_{sc} / I_0 \right] / 2.303$$
$$\approx \left( \sum I_{sc} / I_0 \right) / 2.303$$

$$\left( \sum I_{sc} / I_0 \ll 1 \right)$$

where A is the apparent absorbance of dispersion at wavelength λ. $I_t$ and $I_0$ are the intensities of transmitted and incident light, respectively. The numerical value 2.303 is needed as a conversion factor when natural logs are replaced by base 10 logarithms. Σ indicates the sum of the all scattered light at all directions. Thus, $$\log A = \log \Sigma I_{sc} + C_1$$

where $C_1$ is a constant. If we assume that m is only particle size dependent, from $I_{sc} = k/\lambda^m$ and $\log A = \log \Sigma I_{sc} + C_1$, then we have $$\log A = -m \log \lambda + C_2$$

where $C_2$ is a constant for a given dispersion system and given absorbance measurement setup. Thus, we have $$m = -(d \log A / d \log \lambda) = -(d \ln A / d \ln \lambda)$$

where m is a relative particle size dependent scattering index or PSRSI.

To calculate the PSRSI, the spectrum of the dispersion to be tested is scanned over a predetermined wavelength range. From the spectrum, the optimal working wavelength for the dispersion is selected from the predetermined wavelength range. Reiterations may be used to determine the optimal working wavelength suitable for an actual system, taking into account the possible deviations of that system. Dilution and proper stabilizers may be needed for the reiterations.

To determine the optimal working wavelength, the selected wavelength λ includes the following: (i) 0.1<PS/λ<1, where PS is the particle size of interest; (ii) there is no absorption at or near the selected wavelength λ, the apparent absorbance should be mainly due to the light scattering of the dispersion; (iii) at or near the selected wavelength λ, the rate of its apparent absorbance change with wavelength is not negligible (e.g., should be large enough so that the spectrophotometer's measurement accuracy is high enough to provide meaningful accuracy of PSRSI); and (iv) generally, the concentration of dispersions to be scanned should fall in the range for which apparent absorbance at designated wavelength is from about 0.2 to about 2.0. In a tighter specification, the range is from about 0.4 to about 0.5, to achieve better reproducibility. In embodiments, the PS is from about 40 nm to about 1200 nm, or from about 90 nm to about 800 nm.

In embodiments, a method is provided for evaluating particle size of a colorless or light color pigment dispersion by using the PSRSI. The method comprises preparing pigment dispersion having a known particle size and comprising a dispersion of colorless or light color particles in a fluid. The spectrum of the pigment dispersion is evaluated over a predetermined wavelength range by collecting transmission intensity over the predetermined wavelength at a fixed angle (e.g., 0° for a UV-Vis spectrophotometer), and selecting a wavelength from the predetermined wavelength range wherein the selected wavelength λ meets the specific characteristics described above for optimal working wavelength. In embodiments, the predetermined wavelength range spans about 50 nm. The range is selected based on the following considerations: (1) PSRSI is wavelength-dependent and, as such, the range should not be too large; and (2) the accuracy of PSRSI calculation is dependent on the accuracy of the absorbance, and more specifically, the rate of change of absorbance with wavelength change. As such, the wavelength range should not be too small. Next, a particle size related scattering index of the pigment dispersion is calculated, wherein the particle size related scattering index is calculated from the following equation:

$$-(d \log A / d \log \lambda),$$

wherein A is an absorbance value of the pigment dispersion at the selected wavelength λ. The particle size related scattering index (PSRSI) can directly be used, as a measure of the particle size, to compare with the target values for dispersion characterization and qualification. The particle size related scattering index of the pigment dispersion can also be used to build a calibration curve to correlate the particle size related scattering index and relative particle size (PS/λ) of the pigment dispersion, and be used for comparing a particle size related scattering index of a sample of the pigment dispersion having an unknown particle size against the calibration curve to determine the relative particle size of the sample. The particle size related scattering index of a pigment dispersion allows one to correlate, either directly or indirectly, with the particle size of the pigment dispersion.

The calibration curve of the pigment dispersion may be plotted as a function of relative particle size by repeating the following: evaluating a spectrum of a pigment dispersion over a predetermined wavelength range by collecting transmission intensity over the predetermined wavelength at a fixed angle (e.g., 0° for UV-Vis spectrophotometer), selecting a wavelength from the predetermined wavelength range wherein the selected wavelength λ is selected based on the specific characteristics described above for optimal working wavelength, and calculating the particle size related scattering index of the pigment dispersion, wherein the method is repeated for multiple samples of the pigment dispersion having different particle sizes. In another embodiment, the plot may be built, after evaluating the spectrum of the pigment dispersion over the predetermined wavelength range, by repeating the following: selecting a wavelength from the predetermined wavelength range wherein the selected wavelength λ is selected based on the specific characteristics described above for optimal working wavelength, and calculating the particle size related scattering index of the pigment dispersion, wherein the method is repeated for the pigment dispersion at multiple wavelengths.

In yet another embodiment, the calibration curve is built by repeating the following: evaluating a spectrum of a pigment dispersion over a predetermined wavelength range by collecting transmission intensity over the predetermined wavelength at a fixed angle (e.g., 0° for UV-Vis spectrophotometer), selecting a wavelength from the predetermined wavelength range wherein the selected wavelength λ is selected based on the specific characteristics described above for optimal working wavelength, and calculating the particle size related scattering index of the pigment dispersion, wherein the method is repeated for multiple samples of the pigment dispersion being subjected to different processing times.

Subsequently, a particle size related scattering index of a sample of the pigment dispersion, having an unknown particle size, is calculated at the selected wavelength λ, and compared against the calibration curve calculated for the pigment dispersion to determine the relative particle size of the sample of the pigment dispersion and alternatively, to determine whether the sample meets a target particle size.

In embodiments, the sample of the pigment dispersion is subjected to further processing or reduction in particle size if the sample dispersion does not meet the target or desired particle size. The further processing is repeated until the sample has a particle size related scattering index that is substantially similar to a particle size related scattering index on the calibration curve that correlates with a desired or target particle size. In some embodiments, the pigment dispersion or its samples are diluted prior to evaluation. In further embodiments, a stabilizer is included into the pigment dispersion or its samples prior to evaluation of its spectrum. Dilution may be needed for a variety of reasons, such as for example, avoiding multiple scattering, avoiding inter-particle interaction, and avoiding a particle size aggregation that is too large (where the light scattering is very significant). Also, dilution is maybe needed to maintain the apparent absorbance within the range of 0.2~2. In some dispersions, simple dilution with solvent may destabilizes the dispersion, and the particles tend to aggregate together. In this case, a stabilizer may be needed.

In another embodiment, the method described herein is automated. In such embodiments, dilute solutions should be used. As shown in FIG. 1, a system 30 may automate the calculation of PSRSI for pigment dispersions. For example, a data carrier carrying computer readable instructions configured such that when the computer readable instructions are executed, the computer readable instructions cause a computer 25 to evaluate a spectrum of a colorless or light color pigment dispersion over a predetermined wavelength range by collecting transmission intensity over the predetermined wavelength at a fixed angle, and select a wavelength from the predetermined wavelength range based on the specific characteristics described above for optimal working wavelength. A sample of the colorless or light color pigment dispersion 5, with known particle size, is evaluated for its spectrum over a predetermined wavelength range by a spectrophotometer 10. The spectrometer 15 produces the light of the selected color correlating to the predetermined wavelengths and a photometer 20 measures the intensity of light transmitting the sample dispersion at angle zero or the intensity of light being scattered by the sample dispersion 5 at other fixed angle. The collected intensity data is subsequently transmitted to the computer 25 which calculates the PSRSI according to the equation (1) from the data collected by and received from the spectrophotometer 10. The PSRSI can be used by the computer to build a calibration curve with which to compare against other samples of the pigment dispersion to determine whether the sample being evaluated meets a target particle size, e.g., whether the PSRSI of the pigment dispersion sample being evaluated is substantially similar to a PSRSI that correlates to a target particle size. The calibration curve may be built according to the embodiments described previously. The computer may indicate when the target size is met or instruct further processing until the target size is met. In embodiments, the spectrophotometer can be a UV-Vis spectrophotometer, an IR spectrophotometer, a Visible-Near IR spectrophotometer, or a Raman spectrophotometer, depending on sample spectral properties and particle size. When a conventional UV-Vis spectrophotometer is used, due to the requirement of $0.1<PS/\lambda<1$, suitable results may be limited to particle sizes from about 40 nm to about 1200 nm. If a spectrophotometer of other wavelength is used, such as an IR spectrophotometer, suitable results may be obtained over a broader range of particle size, such as for example, from about 100 nm to about 5000 nm. If a Raman spectrophotometer is used, the fixed angle at which scattering light intensity is collected is a measurement other than zero degrees (e.g., 90°), and the relative intensity of scattering light ($I_{sc}/I_0$) is measured rather than the apparent absorbance. In this case, $I_{sc}/I_0$ may be smaller than 0.2. The concentration of the sample for optimal measurement depends on the sensitivity of the spectrometer and can be determined experimentally.

The computer 25 may be a remote computer that receives the intensity data from the spectrophotometer either by wired or wireless means. Wireless means may include, by no way in limitation, RF, infrared (IR), Bluetooth, ZigBee, and other 802.15 protocols, 802.11 WiFi, spread spectrum communication and frequency hopping communication. Embodiments that use multiple frequencies can facilitate better communication because the sensor can continually switch frequencies until it finds the strongest frequency in the area with which to communicate.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLE

The example set forth herein below and is illustrative of different compositions and conditions that can be used in practicing the present embodiments. All proportions are by weight unless otherwise indicated. It will be apparent, however, that the embodiments can be practiced with many types of compositions and can have many different uses in accordance with the disclosure above and as pointed out hereinafter.

Example 1

Latex Dispersions

Figure 2:
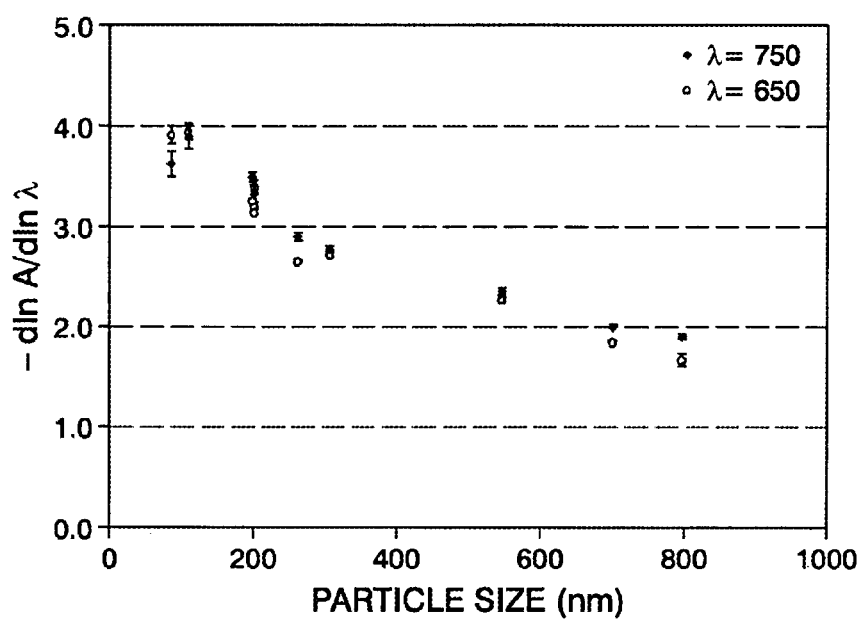
FIG. 2 is a graph showing the PSRSI at different wavelengths of mono-dispersed latex standards in aqueous solutions.

A series of mono-dispersed latex standards of different size were used as testing samples (e.g., 85, 109, 198, 199, 261, 305, 546, 700 and 797 nm), available from The Dow Chemical Co. (Wilmington, Del.) and Duke Scientific Corp. (Fremont, Calif.). Over the wavelength range between 400 to 1000 nm, there is no absorption peak observed for latex dispersion and the apparent absorbance is mainly the contribution of light scattering due to the existence of latex particles. For each latex dispersion, 4 scans were conducted at different concentrations and the results are shown in FIG. 2. As can be seen, PSRSI is monotonously related to the particle size at each specific wavelength within certain range. Furthermore, in the plot of PSRSI~PS/$\lambda$, the results for two wavelengths coincide with each other, indicating that PSRSI is a PS/$\lambda$ dependent index. Thus, PSRSI can be used as an index for the characterization of particle size. When applied to a poly-dispersed latex system, e.g., part of the EA toner process, PSRSI can also serve as an index for its effective particle size instead of the real particle size.

Example 2

DUC Millbase

Over the wavelength range between 460 and 1000 nm, there is no absorption peak observed for the DUC dispersion millbase. The apparent absorbance is mainly from the contribution of light scattering due to the existence of ZnO particles in dispersion. As shown in FIG. 3, the PSRSI value is monotonously related to the relative particle size within certain range (0.2<PS/$\lambda$<1.0) for a mono-dispersed colloidal system. Similarly, for a poly-dispersed DUC millbase, the parameter PSRSI is monotonously related to an effective particle size and therefore can be utilized as an index for the processing progress and the determination of processing endpoint, e.g., the characterization and qualification of DUC millbase.

Considering the particle size of interest for DUC millbase ranges from 200 to 400 nm, the acceptable wavelength, for which PSRSI value can be used as a parameter for the characterization of dispersion can range from 350 to 1000 nm. Taking other factors into account, such as absorption band range and absorbance measurement accuracy, a wavelength between 500 and 1000 nm, or between 600 and 800 nm, should be chosen. As for the DUC dispersion, a dilution where its absorbance at the selected wavelength is from about 0.2 to about 2.0 is applied. However, a tighter specification such as an absorbance, A, from about 0.4 to about 0.5 is suggested for better reproducibility.

Two sets of DUC millbase samples were taken from the two processing batches at different processing stages for the tests. The spectra of diluted samples were taken on Hitachi U-2000 spectrophotometer over the range from 330 to 1000 nm and PSRSI was calculated at wavelength 650 and 750 nm. Additionally, particle size of each sample was measured by Malvern HPPS particle sizer. The millbase samples were also coated into dry films on 1"×2" micro glass slides at designated thickness and the T20 (transmission at 20 μm thickness) be interpolated. FIG. 4 shows the plot of PSRSI and T20 vs. particle size. It can be seen from FIG. 4 that the method using PSRSI provides more reproducible results ("PSRSI") and better correlation between the measured parameter and particle size with fewer measurements. The measurements of PSRSI took only 1-10 minutes, whereas the T20 measurements took about an hour.

The present embodiments can be applied to other colorless or light color dispersion system as long as there exists a wavelength range ($\Delta\lambda$>~50 nm to allow sufficient accuracy of -d ln A/d ln$\lambda$ calculation) where scattering is the main contributor to the apparent absorbance and the absorption is negligible. One example could be a PTFE-doped CTL dispersion.

All the patents and applications referred to herein are hereby specifically, and totally incorporated herein by reference in their entirety in the instant specification.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A system for evaluating a colorless or light color pigment dispersion, comprising:
    a data carrier for carrying computer readable instructions;
    a computer for executing the computer readable instructions; and
    a spectrophotometer adapted to communicate with the computer for evaluating a spectrum of a pigment dispersion over a predetermined wavelength range by collecting transmission intensity at a fixed angle, wherein the pigment dispersion is colorless or light color, and wherein the executed computer readable instructions cause the computer to
    receive the collected transmission intensity from the spectrophotometer for selecting a wavelength $\lambda$ from the predetermined wavelength range based on the following characteristics: (i) 0.1<PS/$\lambda$<1, wherein PS is a particle size of interest, (ii) there is no absorption at or near the selected wavelength $\lambda$ and apparent absorbance is due to light scattering of the pigment dispersion, (iii) the rate of apparent absorbance change with wavelength is not negligible at or near the selected wavelength $\lambda$, and (iv) a concentration of the pigment dispersion falls in a range for which apparent absorbance at the selected wavelength $\lambda$ is from about 0.2 to about 2.0,
    calculate a particle size related scattering index of the pigment dispersion from the following equation: $-(d \log A/d \log \lambda)$, wherein A is an absorbance value of the pigment dispersion at the selected wavelength $\lambda$,
    build a calibration curve to correlate the particle size related scattering index and relative particle size of the pigment dispersion,
    compare a particle size related scattering index of a sample of the pigment dispersion having an unknown particle size against the calibration curve to determine a relative particle size of the sample, and
    indicate the relative particle size of the sample.

2. The system of claim 1, wherein the concentration of the pigment dispersion falls in a range for which apparent absorbance at the selected wavelength $\lambda$ is from about 0.4 to about 0.5.

3. The system of claim 1, wherein the PS is from about 100 nm to about 5000 nm.

4. The system of claim 1, wherein the computer instructs further processing of the sample until a target particle size is achieved.

5. The system of claim 1, wherein the spectrophotometer communicates wirelessly or by wire with the computer.

6. The system of claim 3, wherein the PS is from about 40 nm to about 1200 nm.

7. The system of claim 6, wherein the PS is from about 90 nm to about 800 nm.

8. The system of claim 1, wherein the calibration curve plots the particle size related scattering index of the pigment dispersion as a function of relative particle size for multiple samples of the pigment dispersion having different particle sizes.

9. The system of claim 1, wherein the calibration curve plots the particle size related scattering index of the pigment dispersion as a function of relative particle size for the pigment dispersion at multiple wavelengths.

10. The system of claim 1, wherein the calibration curve plots the particle size related scattering index of the pigment dispersion as a function of processing time for the pigment dispersion at different processing times.

11. The system of claim 1, wherein the sample of the pigment dispersion is subjected to further processing until a target particle size is achieved.

12. The system of claim 1, wherein the predetermined wavelength range spans about 50 nm.

13. The system of claim 1, wherein the pigment dispersion is diluted prior to evaluation of its spectrum.

14. The system of claim 1, wherein a stabilizer is included into the pigment dispersion prior to evaluation of its spectrum.

15. The system of claim 1, wherein the spectrophotometer is selected from the group consisting of a UV-Vis spectrophotometer, an IR spectrophotometer, a Visible-Near IR spectrophotometer and a Raman spectrophotometer.

16. The system of claim 1 being automated.

* * * * *